United States Patent [19]

Horodysky et al.

[11] Patent Number: 4,704,218
[45] Date of Patent: * Nov. 3, 1987

[54] REACTION PRODUCTS OF SULFUR CONTAINING VICINAL DIOLS AND HYDROGEN PHOSPHITES AS LUBRICANT AND FUEL ADDITIVES

[76] Inventors: Andrew G. Horodysky, 139 Weston Dr., Cherry Hill, N.J. 08003; Phillip S. Landis, 5733 Independence Cir., Alexandria, Va. 22312

[*] Notice: The portion of the term of this patent subsequent to Jun. 11, 2002 has been disclaimed.

[21] Appl. No.: 809,678

[22] Filed: Dec. 16, 1985

[51] Int. Cl.[4] .............. C10M 135/24; C10M 137/10
[52] U.S. Cl. .................. 252/46.6; 252/49.9; 44/53; 44/76; 558/83; 558/118; 558/177; 558/183
[58] Field of Search ............... 252/46.6, 49.9, 32.7 R, 252/32.7 E; 44/76, 53; 558/83, 118, 177, 183

[56] References Cited

U.S. PATENT DOCUMENTS

| | | |
|---|---|---|
| 3,649,538 | 3/1972 | Hotten . |
| 3,899,433 | 8/1975 | Unick et al. . |
| 4,356,097 | 10/1982 | Papay . |
| 4,394,276 | 7/1983 | Small, Jr. .............. 252/32.7 E |
| 4,394,277 | 7/1983 | Small, Jr. . |
| 4,406,803 | 9/1983 | Liston et al. .............. 252/32.7 E X |
| 4,522,629 | 6/1985 | Horodysky et al. . |
| 4,532,057 | 7/1985 | Horodysky et al. . |
| 4,563,293 | 1/1986 | Small, Jr. .............. 252/32.7 E |

Primary Examiner—William R. Dixon, Jr.
Assistant Examiner—E. McAvoy
Attorney, Agent, or Firm—Alexander J. McKillop; Michael G. Gilman; Edward J. Trojnar

[57] ABSTRACT

The reaction product of a long chain vicinal diol containing at least 10 carbon atoms and at least one sulfur atom in the chain, with dihydrocarbyl hydrogen phosphites are effective friction reducing antiwear additives in lubricating oils, greases and fuels.

15 Claims, No Drawings

REACTION PRODUCTS OF SULFUR CONTAINING VICINAL DIOLS AND HYDROGEN PHOSPHITES AS LUBRICANT AND FUEL ADDITIVES

BACKGROUND OF THE INVENTION

Alcohols and diols are well known for their surfactant and lubricity properties when formulated into lubricating oils, and for their water-scavenging characteristics when blended into fuels. Vicinal hydroxyl-containing alkyl carboxylates, such as glycerol monooleate, found widespread use as lubricity additives. The use of certain long chain hydrocarbyl vicinal diols has been reported by Hotten in U.S. Pat. No. 3,649,538 and Unick et al in U.S. Pat. No. 3,899,433.

Phosphorus-containing lubricating additives have also found widespread use. Phosphonates have been found to be lubricity agents as exemplified by Papay in U.S. Pat. No. 4,356,097 in which the use of dihydrocarbyl hydrocarbyl phosphonates in lubricant formulations is disclosed.

Borated sulfur containing 1,2-alkane diols are disclosed in U.S. Pat. No. 4,394,277 as lubricating oil additives. The reaction products of 1,2-alkane diols and dihydrocarbyl hydrogen phosphites as lubricant additives are disclosed in U.S. Pat. No. 4,532,057, and their use as intermediates for subsequent boration is disclosed in U.S. Pat. No. 4,522,629, both of which are incorporated herein by reference.

SUMMARY OF THE INVENTION

The reaction products of long chain vicinal diols containing at least 10 carbon atoms and one or more sulfur atom in the chain, with a dihydrocarbyl hydrogen phosphate containing 1 to 6 carbon atoms in each hydrocarbyl group are effective friction-reducing antiwear additives in lubricating oils, greases and fuels.

DETAILED DESCRIPTION OF THE INVENTION

Because of the relatively complex nature of the reaction that occurs when phosphites and vicinal diols are interacted, no precise structure can be assigned to the product. Thus, the final product will be referred to herein, both in the specification and the claims, as the product of the specified reaction.

However, it is believed that the reaction products comprise at least some of the compounds described below.

Long-chain sulfur-containing vicinal diols are converted to their corresponding hydrogen phosphite derivatives or partial hydrogen phosphite derivatives by reaction with molar amounts or less than molar amounts of low molecular weight dialkyl hydrogen phosphite as exemplified below.

$$R-S_x-R'(OH)_2 + (R''O)_2\overset{O}{\underset{\|}{P}}-H \xrightarrow{\Delta}$$

Where,
R is $C_8$-$C_{30}$ hydrocarbyl, preferably $C_{10}$ to $C_{20}$ hydrocarbyl;
R' is $C_2$-$C_6$ hydrocarbylene;
R'' is $C_1$-$C_6$ hydrocarbyl; and
x is an integer from 1 to 3, preferably 1.

Specifically, where $$R'(OH)_2 = (CH_2)_y - \underset{OH}{\underset{|}{CH}} - \underset{OH}{\underset{|}{CH_2}}$$

and y is an integer from 1-6, preferably 1;

$$R-S-(CH_2)_y-\underset{OH}{\underset{|}{CH}}-\underset{OH}{\underset{|}{CH_2}} + (R''O)_2-\overset{O}{\underset{\|}{\underset{|}{P}}}-H \xrightarrow[-R''OH]{\Delta}$$

[Schemes showing reaction products including cyclic phosphite, monophosphite, and bisphosphite structures]

plus similar products and oligomers of similar products.

The dialkyl hydrogen phosphite starting material can be used in up to molar amounts per mole of long-chain sulfur containing vicinal diol. Less than molar amounts of the phosphite such as 0.33 to 0.5 moles per mole of diol are preferred. The partial phosphates appear to exhibit much greater frictional activity than the fully converted product.

The sulfur-containing diols can be easily made using known methods. Dihydroxy alkyl sulfides can be derived by the reaction of mercaptan or sodium alkyl mercaptide with 1-halopropanediol as shown below.

$$RSH + X-(CH_2)_y-\underset{OH}{\underset{|}{CH}}-\underset{OH}{\underset{|}{CH_2}} \xrightarrow{-HZ}$$

$$R-S-(CH_2)_2-\underset{OH}{\underset{|}{CH}}-\underset{OH}{\underset{|}{CH_2}}$$

Alternately, these may be prepared by the reaction of alkyl halides with sodium or potassium glycerol 1-mercaptide. Additionally, the sulfur-containing diols can be prepared by the reaction of mercaptan RSH with glycidol at elevated temperatures optionally in the presence of a trialkylamine catalyst.

Examples of RSR'(OH)$_2$ include 1,2-dihydroxypropane octadecyl sulfide, 1,2-dihydroxypropane dodecyl sulfide, 1,2-dihydroxypropane octyl sulfide, 1,2-dihydroxypropane hexadecyl sulfide, 1,2-dihydroxypropane pentadecyl sulfide, 1,2-dihydroxypropane tridecyl sulfide, similar sulfides, and mixtures of the above and similar sulfides.

The reaction products of sulfur containing vicinal diols and phosphites described above can be subsequently borated in the manner described in U.S. Pat. No. 4,522,629 which is incorporated herein by reference. When the reaction product is prepared for further boration it is desirable to use a molar excess of the diol so that sufficient hydroxyl groups will be available for boration. For example, ratios of diol to phosphite of 4:1 to 2:1 would be suitable.

The compounds of the invention are used with lubricating oils or greases to the extent of from about 0.1% to about 10% by weight of the total composition, preferably from about 0.2% to about 2% and with fuels to the extent of from about 5 lbs. to about 250 lbs. per 1000 bbls. of fuel. Furthermore, other additives, such as detergents, antioxidants, antiwear agents and the like may be present. These can include phenates, sulfonates, polymeric succinimides, zinc dialkyl or aryl dithiophosphates, polymers, calcium and magnesium salts, polymeric viscosity index improving additives such as olefin copolymers, sulfurized olefins and the like.

The lubricants contemplated for use with the additives herein disclosed include mineral and synthetic hydrocarbon oils and synthetic oils and greases from any of these, including the mixtures. The synthetic hydrocarbon oils include long-chain alkanes such as cetanes and olefin polymers such as oligomers of hexane, octene, decene, and dodecene, etc. These vicinal diol-derived phosphites are especially effective in synthetic oils formulated using mixtures of synthetic hydrocarbon olefin oligomers and lesser amounts of hydrocarbyl carboxylate ester fluids. The other synthetic oils, which can be used alone with the phosphorus compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, aleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salt and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening agents comprise substituted ureas, phtalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals into the surface of the clay particles; prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 to 15 percent by weight of the total grease composition.

The liquid fuels contemplated include the liquid hydrocarbons, such as gasoline, fuel oil and diesel oil and the liquid alcohols such as methyl alcohol and ethyl alcohol. The fuels also include mixtures of alcohols as well as mixtures of alcohols and liquid hydrocarbons. The fuel compositions of this invention comprise a major amount of a liquid fuel and a minor amount of the additives described above.

The invention is illustrated by the following non-limiting examples in which all parts are by weight unless otherwise stated.

EXAMPLE 1

1,2-Dihydroxypropane Hexadecyl Sulfide-Derived Phosphite

Approximately 199 g of 50% aqueous sodium hydroxide solution was added dropwise over a period of 1¼ hours to a solution of hexadecyl mercaptan (641 g) and 1-chloropropane-2,3-diol (275 g) in isopropanol solvent (750 ml), at ambient temperature. The reaction temperature rose from 25° C. to 75° C. during the addition. The reaction was refluxed for six hours at 83° C. and then filtered hot through paper to remove the precipitated salt. The isopropanol solvent was removed by distillation. The product residue was dissolved in about 2,000 ml toluene and washed with water several times. The toluene solution was dried over magnesium sulfate and filtered through diatomaceous earth. Toluene was removed by high-speed rotary evaporation to yield a white solid product.

Approximately 111 g of the above 1,2-dihydroxypropane hexadecyl sulfide was placed in a glass reactor equipped with heater, agitator, Dean-Stark tube with condenser, and provision for blanketing and vapor space with nitrogen. The contents were heated to about 70° C. to liquify and 12 g of dimethyl hydrogen phosphite was slowly added. The reaction mixture was heated to 110° C. during 1 hour and held at 110° C. for 2 hours, held at 120° C. for 1 hour and held at 130° C. for 1 hour. During this reaction period, methanol distilled over and was collected in the trap. The crude product was vacuum-distilled removing volatile materials producing about 117 g of finished additive.

EXAMPLE 2

1,2-Dihydroxypropane Hexadecyl Sulfide-Derived Phosphite

Approximately 111 g of 1,2-dihydroxypropane hexadecyl sulfide, prepared as described in Example 1, was placed in a reactor equipped as generally described in Example 1. The contents were heated to 70° C. to liquify and 36 g dimethyl hydrogen phosphite was slowly added. The temperature was raised to 110° C. over a period of 1 hour and held at 110° C. for 2 hours, held at 130° C. for 1 hour. During this reaction period, methanol distilled over and was collected in the trap. The crude product was vacuum-distilled removing volatile materials.

EXAMPLE 3

1,2-Dihydroxypropane Dodecyl Sulfide Phosphite

Approximately 397 g of 50% aqueous sodium hydroxide solution was added dropwise over a period of 7 hours to a solution of n-dodecyl mercaptan (1000 g) and 1-chloropropane-2,3-diol (547 g) in isopropanol solvent (2000 cc) at ambient temperature. The reaction temperature rose from 20° to 56° C. during the addition. The reaction was refluxed for 5 hours at 80° C. and then filtered hot through paper to remove the precipitated salt. The isopropanol solvent was removed by distillation. The product residue was dissolved in about 4000 cc toluene and washed with water several times. The toluene solution was dried over magnesium sulfate and filtered through diatomaceous earth. Toluene was removed by high-speed rotary evaporation to yield a white solid product.

Approximately 100 g of the above 1,2-dihydroxypropane dodecyl sulfide was reacted with 15 g dimethyl hydrogen phosphite as generally described in Example 1 until methanol evolution ceased. The product was vacuum-distilled to remove volatile materials.

The sulfur-containing diol-derived phosphites were blended into fully formulated synthetic and mineral oil-based automotive engine oil lubricants and evaluated using the Low Viscosity Friction Apparatus Test. The use of only 2% of the product of Example 1 reduced the coefficient of friction by 30% as shown in Table 2.

TABLE 1

| Friction Test Results Using Low Velocity Friction Apparatus | | |
|---|---|---|
| | Additive Conc. in Base Fluid | % Reduction in Coefficient of Friction at |
| | Wt % | 5 Ft/Min | 30 Ft/Min |
| Base Fluid A (fully formulated mineral oil-based automotive engine oil containing detergent/dispersant/inhibitor performance package) SAE 10W-40 | — | 0 | 0 |
| Example 1 | | | |
| 1,2-Dihydroxypropane Hexadecyl Sulfide-Derived Phosphite | 2 | 24 | 19 |
| | 1 | 24 | 11 |

TABLE 2

| Friction Test Results Using Low Velocity Friction Apparatus | | |
|---|---|---|
| | Additive Conc. in Base Fluid | % Reduction in Coefficient of Friction of |
| | Wt % | 5 Ft/Min | 30 Ft/Min |
| Base Fluid B (fully formulated synthetic oil-based automotive engine oil containing detergent/dispersant/inhibitor performance package) SAE 5W-30 | — | 0 | 0 |
| Example 1 | | | |
| 1,2-Dihydroxypropane Hexadecyl Sulfide-Derived Phosphite | 2 | 30 | 27 |
| Example 2 | | | |
| 1,2-Dihydroxypropane Hexadecyl Sulfide-Derived Phosphite | 2 | 20 | 22 |

The results clearly show the friction-reducing properties of the phosphite derivatives.

The products of Example 3 were blended into mineral oil at 1% concentration and evaluated using the Four-Ball Wear Test using a 60 kg load at 1500 rpm for 30 minutes as shown in Table 3.

TABLE 3

| Four-Ball Wear Test Results | | |
|---|---|---|
| | Additive Concentration | Scar Diameter, mm (60 kg load, 1500 rpm 30 min.) |
| | Wt % | 175° F. | 275° F. |
| Base Oil C (Mixture of 80% solvent paraffinic bright at 20% 200-second solvent paraffinic neutral lubricating oils) with 0.2% dibutyl hydrogen phosphite additionally added. | — | 0.6 | 1.3 |
| Example 3 | | | |
| 1,2-Dihydroxypropane-dodecyl sulfide phosphite | 1 | 0.5 | 0.7 |

The results clearly demonstrate the antiwear effectiveness of the phosphite additive of this invention.

Although the present invention has been described with preferred embodiments, it is to be understood that modifications and variations can be resorted to without departing from the spirit and scope of this invention, as those skilled in the art will readily understand. Such variations and modifications are considered to be within the purview and scope of the appended claims.

I claim:

1. A product of the reaction of a long chain vicinal diol containing at least 10 carbon atoms and at least one sulfur atom in the chain with a dihydrocarbyl hydrogen phosphite containing 1 to 6 carbon atoms in each hydrocarbyl group; in which the molar ratio of the vicinal diol: dihydrocarbyl hydrogen phosphite is about 3:1 to about 1:1.

2. The product of claim 1 in which said vicinal diol has the formula $$R-S_x-R'(OH)_2$$

and said dihydrocarbyl hydrogen phosphite has the formula $$(R''O)_2-\overset{\overset{\displaystyle O}{\|}}{P}-H$$

in which
R is $C_8-C_{30}$ hydrocarbyl;
R' is $C_2-C_6$ hydrocarbylene;
R'' is $C_1-C_6$ hydrocarbyl;
x is an integer from 1 to 3.

3. The product of claim 2 in which the vicinal diol has the formula $$R-S_x-(CH_2)_y-\underset{\underset{\displaystyle OH}{|}}{CH}-\underset{\underset{\displaystyle OH}{|}}{CH_2}$$

and y is an integer from 1 to 4.

4. The product of claim 2 in which R is $C_{10}$ to $C_{20}$ hydrocarbyl; and x is 1.

5. The product of claim 3 in which R is $C_{10}$ to $C_{20}$ hydrocarbyl; and x is 1.

6. A lubricant composition comprising a lubricating oil or grease containing a friction reducing amount of the product of claim 1.

7. A lubricant composition comprising a lubricating oil or grease containing a friction reducing amount of the product of claim 2.

8. A lubricant composition comprising a lubricating oil or grease containing a friction reducing amount of the product of claim 3.

9. A lubricant composition comprising a lubricating oil or grease containing a friction reducing amount of the product of claim 4.

10. A lubricant composition comprising a lubricating oil or grease containing a friction reducing amount of the product of claim 5.

11. A fuel composition comprising a major amount of a liquid fuel and a minor amount of the product of claim 1.

12. A fuel composition comprising a major amount of a liquid fuel and a minor amount of the product of claim 2.

13. A fuel composition comprising a major amount of a liquid fuel and a minor amount of the product of claim 3.

14. A fuel composition comprising a major amount of a liquid fuel and a minor amount of the product of claim 4.

15. A fuel composition comprising a major amount of a liquid fuel and a minor amount of the product of claim 5.

* * * * *

UNITED STATES PATENT AND TRADEMARK OFFICE
CERTIFICATE OF CORRECTION

PATENT NO. : 4,704,218

DATED : November 3, 1987

INVENTOR(S) : A.G. Horodysky and P.S. Landis

It is certified that error appears in the above-identified patent and that said Letters Patent is hereby corrected as shown below:

On the title page  Insert

--(73) Assignee: Mobil Oil Corporation, New York, NY --.

Signed and Sealed this

Fifth Day of July, 1988

Attest:

DONALD J. QUIGG

Attesting Officer

Commissioner of Patents and Trademarks